United States Patent [19]
Durand et al.

[11] Patent Number: 5,442,447
[45] Date of Patent: Aug. 15, 1995

[54] DETECTOR FOR THE CONTACTLESS MEASUREMENT OF CHARACTERISTICS OF A LINEAR PRODUCT OF VERY GREAT LENGTH RELATIVE TO ITS OTHER DIMENSIONS, ON A PRODUCTION MACHINE OR THE LIKE

[75] Inventors: Bernard Durand, Pfastatt; Robert Enderlin, Morschwiller le Bas; Pierre Henry, Illzach, all of France

[73] Assignee: Superba, S.A., Mulhouse, France

[21] Appl. No.: 191,290

[22] Filed: Feb. 3, 1994

[30] Foreign Application Priority Data

Feb. 3, 1993 [FR] France .................. 93 01330

[51] Int. Cl.⁶ .................................................. G01N 21/89
[52] U.S. Cl. ........................... 356/429; 250/559.19; 356/430
[58] Field of Search ..................... 356/429–431; 250/571, 572

[56] References Cited

U.S. PATENT DOCUMENTS 4,490,618  12/1984  Cielo ................................. 250/571
5,291,024   3/1994  Barea .............................. 356/429 X

FOREIGN PATENT DOCUMENTS 0493050   7/1992  European Pat. Off. .
3803353   8/1989  Germany .
 680310   7/1992  Switzerland .
1608270  11/1990  U.S.S.R. .

OTHER PUBLICATIONS

R. Leuenberger, "Fadenspannungen beruhrungslos ermitteln", *Melliand Textilberichte*, vol. 73, No. 8, Aug. 1992, pp. 611–613.

Primary Examiner—Vincent P. McGraw
Attorney, Agent, or Firm—Young & Thompson

[57] ABSTRACT

The present invention relates to a detector for measuring the characteristics of a linear product of very great length relative to its other dimensions, on a production machine or the like. The detector operates without contact with the linear product and is provided with at least one means (1) having zones (2 and 3) for measurement relative to a mean position of the moving filament (4) and measuring the variation of the complex morpho-dimensional and/or positional characteristics of the filament (4), this latter varying, either by vibrating movement, or by displacement induced by the mean position of the axis of movement. The invention is applicable to the field of the measurement of the characteristics of linear products of very great length.

24 Claims, 6 Drawing Sheets

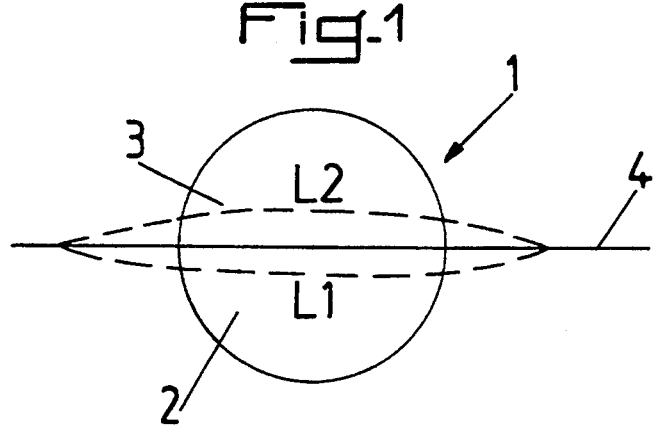
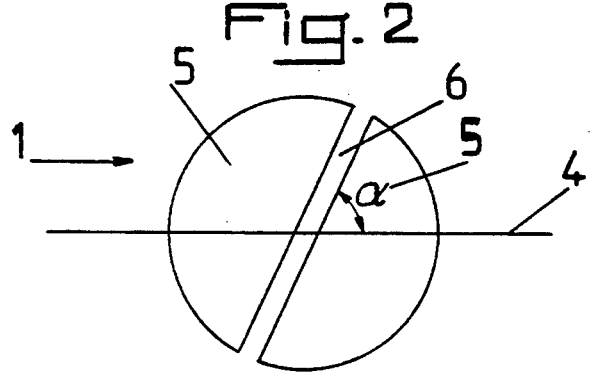
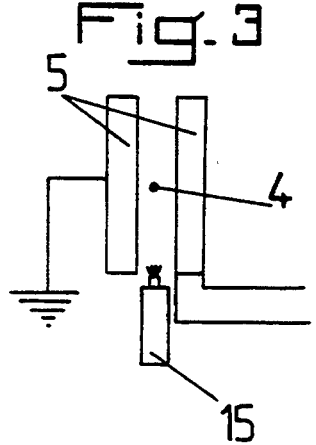

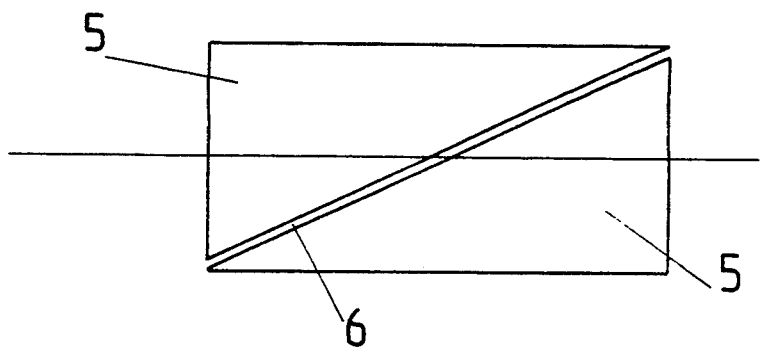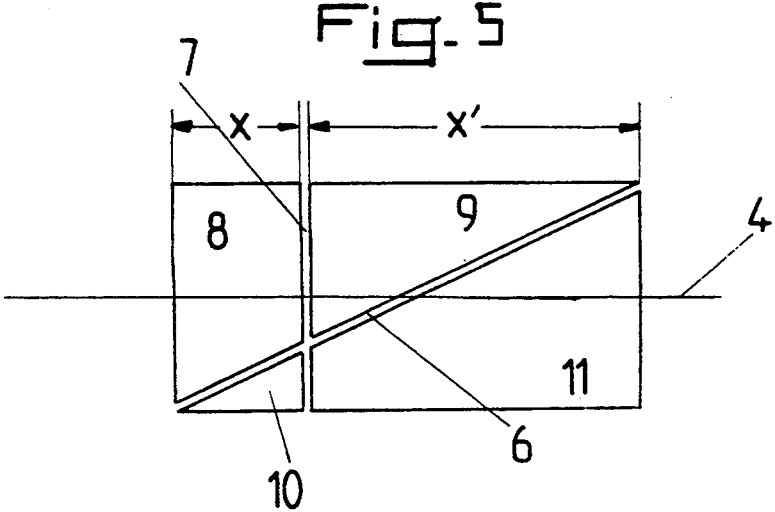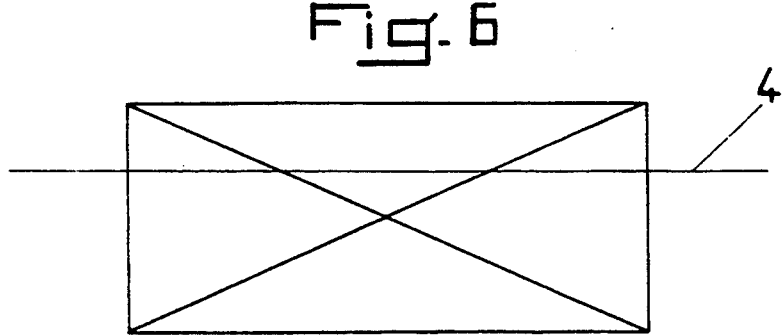

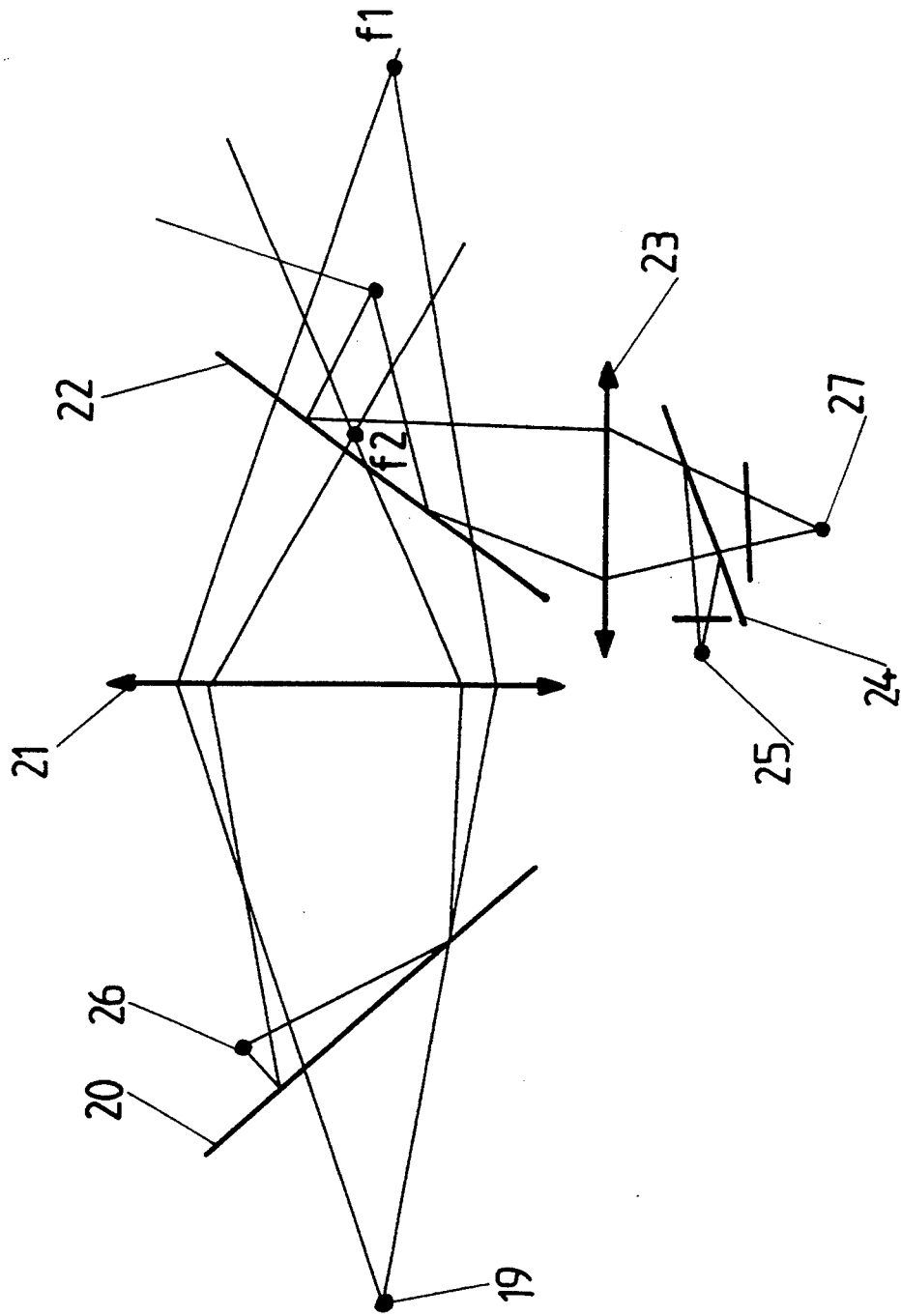

DETECTOR FOR THE CONTACTLESS MEASUREMENT OF CHARACTERISTICS OF A LINEAR PRODUCT OF VERY GREAT LENGTH RELATIVE TO ITS OTHER DIMENSIONS, ON A PRODUCTION MACHINE OR THE LIKE

BACKGROUND OF THE INVENTION

1. Field of the Invention

The present invention relates to the field of the control of linear products of very great length relative to their other dimensions, namely of products in the form of filaments, yarns, ribbons or cloth and has for its object a detector for the contactless measurement of the morpho-dimensional and dynamic characteristics of such a product on a production machine or the like.

2. Description of the Related Art

The knowledge of the characteristics of a product in the form of filament, yarn, ribbon or cloth is particularly necessary in the field of spinning for the verification of the regularity of a given product, namely to detect the possible defects due either to malfunction of the machine or to defectiveness of an element of the machine, or to irregularity or non-homogeneity of the material itself that is used, namely, the filament, yarn, ribbon or cloth.

Moreover, in the field of weaving textile filaments or the like or also in the field of winding metallic wires, there is also a problem of instantaneous recognition of the characteristics of said filaments, particularly their tension and/or their speed and/or their torsion and/or their regularity.

This knowledge of the characteristics of the linear products is particularly applicable to all the sectors of the textile industry, such as spinning, spinning synthetic fibers, winding, warping and weaving.

At present, the measurements of the essential characteristics of the linear products of this type are generally effected by mechanical, electrical or electromagnetic means, by contact, namely, for measurement of speed, at least one wheel mechanism connected to a counter, and as to the tension, by means of a wheel device mounted on a tensioned arm connected to a weighing device.

These known means, however, have the drawback of being in contact with the filament, of needing a wheel, of passing the filament along a sinuous path with the need to tension it, which induces friction, bending, torsion, etc. . . . , and thus imposing supplemental parasitic tensions on said filament.

Moreover, these known means can lead to the formation of fluff and dust and modify the characteristics of the product by friction and heating.

Finally, it is also possible that, upon a breakdown of the machine or the elements of the machine, or even of the measuring detector itself from fluff and dust, to produce blockages of the product to be measured or to be controlled and/or the adhesives of the materials by adherence or fusion (in the case of high speeds), because of the material constituting the product to be measured or the chemical products used for producing the filament, such as textile oil for example.

At present, for example, the measurement of the torsion is possible only by withdrawing and destructive testing of specimens. Such a measurement is not possible on a product in movement. Similarly, the measurement of the fundamental characteristics of a product of great length, such as a textile filament, for example in movement, which are the speed and tension, cannot be effected at present other than by placing a detector in contact with the product, as indicated above.

It is also known to effect measurements of the regularity of the mass or size, for example of filaments, by means of capacitative or optical detectors permitting, in this case, to effect contactless measurements either on the production means, or on specific machines, for example laboratory apparatus.

Thus there is known, from FR-A-2 549 096, a process for automatic control of textile filaments and an apparatus for practicing this process, permitting automatically effectuating, with the aid of a single and same apparatus, a group of measurements on at least one sample of filament, these measurements being conceived to permit at least one determination of the titer of this filament and a determination of its regularity as to linear mass, and/or at least one determination of the torsion and a determination of the dynamometric properties of this filament. According to this reference, the measurements are repeated on a series of specimens of the same filament and the results are registered, then processed by computer means, for their statistical use and/or their storage.

According to this process and the apparatus for its practice, the measurement of the regularity of the filament is effected by means of a capacitative detector comprising a double condenser comprising a central plate and two lateral plates defining two interstices of which one is traversed by the filament. This process and this apparatus permit obtaining information relative to the regularity of the filament thanks to the capacitative detector and of the titer of this filament thanks to a balance of precision compiling said filament after measurement of its regularity.

From FR-A-2 587 806 is known a device for the continuous measurement of the linear mass of a textile product present in the form of a detector analogous to that for practicing the process according to FR-A-2 549 096, in which are provided means simultaneously modifying the air gap of the two capacitances (condensers) constituting said detector. This detector permits a more precise measurement than earlier detectors.

The capacitative detector measures the mass regularity of the filament, given that the variation of the mass in the air gap of the capacitative detector gives rise to a variation of the dielectric of the condenser formed by the two armatures of this detector, in which the dielectric is constituted by the ambient air and the mass of filament situated between the armatures.

There is also known, from FR-A-2 651 888, a process and an apparatus permitting the characterization and the measurement of the quality of ribbons and yarns or of the filaments of textile fibers.

This process and this device also consist in using specimens and effecting on these latter measurements of regularity, of the breakage force of these specimens, as well as the determination of the titer of said specimens. Such a device permits of course characterizing rapidly a large number of specimens, but it is not at all adapted to continuous measurement, simply because of its construction and the measurement means used. Moreover, the assembly of detectors does not permit determining the speed and the tension of the filament.

Furthermore, in known detectors, it is usual to provide an adjustability of the frequency supply of the capacitance or capacitances as a function of certain physico-chemical parameters, such as humidity.

FR-A-2 657 959 describes a process and a device for the measurement of torsion of a textile filament, in which the filament is illuminated by optical means from a luminous beam, so as to form an illuminated spot corresponding to the light diffracted by the fibers from the surface of the core, this luminous spot being examined so as to analyze the energy distribution so as to define the angle of torsion.

Finally, there is known from FR-A-2 657 958 a process and a device for the measurement of at least one transverse dimension of a textile filament, said process consisting in illuminating the filament with a coherent light beam, examining the interference fringes obtained in the focal plane of an optical system, and deducing the transverse dimension of the distance separating the interference fringes, at least two symmetrical fringes being provided relative to the filament to form two secondary interfering sources, the transverse dimension of the filament being deduced from the spacing between the fringes of the obtained interference figure.

This known process and device permit determining particularly the number of a filament, but, because of the necessary size of the device and its mounting about the filament to be measured, its application to continuous measurement on a production machine or for temporary measurement at the inlet or at the outlet of such a machine cannot be envisaged.

If the recited means permit measurements of regularity and torsion without contact and if, by severe miniaturization, the realization of these measurements were permitted without contact on production machines, none of these means would permit simultaneous contactless measurement of the speed of a linear product, of its mass regularity, absolute or not, of its tension, or of its torsion.

Furthermore, the publication MELLIAND TEXTILBERICHTE, Vol. 73, No. 8, August 1992, HEIDELBERG, pages 611-613, XP294573—LEUENBERGER "Fadenspannungen berührungslos ermitteln" describes a technique for measurement of the tension of a continuous filament to be spun, by measurement of the circular vibration of the filament relative to a guide eyelet for the filament. This measurement is particularly difficult to carry out, because the filament follows a spacial trajectory of large amplitude, such that the addition of a tension detector with loading is inconceivable. The filament is subjected to a circular vibration which causes the appearance of a loop and a node on the forming filament, such that at this region the filament is fragile and the installation of a detector cannot be envisaged.

The circular oscillations of the filament are registered by means of a camera and the vibration node is determined from the curve of the envelope extracted from the registry of said oscillations.

According to this document, the filament is not subjected to any external vibration, the vibration being generated in the course of operation of the machine. The detector considers this vibration and, after processing, deduces from it the tension. However, this detector is not capable of extracting the component of vibration of a filament, even if it is minimal, without contact and displacement of the filament.

OBJECTS AND SUMMARY OF THE INVENTION

The present invention has for its object to overcome the drawbacks of these detectors and these measurement devices known until now, by providing a new generation of novel detectors. These novel detectors can determine simultaneously several or all of the characteristics recited above, by direct individual measurements or by measurements of partial functions, which, by intercorrelation, permit deducing the other characteristics or parameters of a linear product of very great length relative to its other dimensions, on a production machine or the like.

To this end, it has for its object a detector characterized in that it is contactless in operation and in that it is provided with at least one means having measurement zones relative to a mean position of the passing filament and measuring the variation of the complex morpho-dimensional and/or positional characteristics of the filament, this latter varying, either by vibratory movement, or else by displacement induced by the mean position of the axis of movement, the measurement zones having each one sensitivity which is different and variable relative to the medial plane of the axis of the filament to be measured.

BRIEF DESCRIPTION

The invention will be better understood, from the following description, which relates to preferred embodiments, given by way of non-limiting example, and explained with reference to the accompanying schematic drawings, in which:

FIG. 1 is an elevational and/or cross-sectional view on a medial plane of a detector according to the invention;

FIG. 2 is a view analogous to that of FIG. 1, of a modified embodiment of the invention;

FIG. 3 is a side elevational view of the detector according to FIG. 2;

FIGS. 4-10 are views analogous to that of FIG. 2, of different modifications of the embodiment of the detector;

FIGS. 15 and 16 are side elevational views of optical detectors.

DESCRIPTION OF THE PREFERRED EMBODIMENTS

Figure 7:
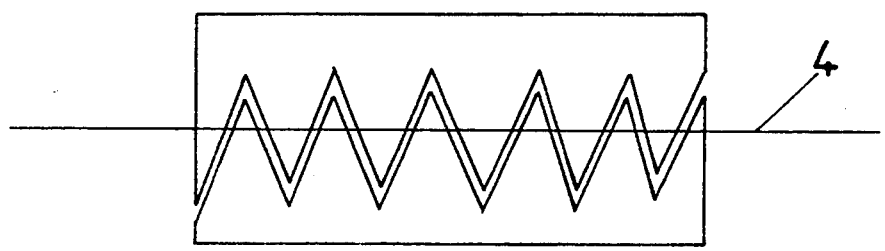

According to the invention, and as shown more particularly in FIGS. 1-16 of the accompanying drawings, the detector for the measurement of the characteristics of a linear product of very great length relative to its other dimensions, on a production machine or the like, operates in a contact-free manner and is provided with at least one means 1 having measuring zones 2 and 3 relative to a mean position of the filament 4 and measuring the variation of the complex morpho-dimensional and positional characteristics of the filament 4, this latter varying, either by vibratory movement, or by induced displacement of the mean position of the axis of movement.

According to a characteristic of the invention, the zones 2 and 3 each have a different and variable sensitivity relative to a medial plane of the axis of the filament 4 to be measured. As a result, a vibration of the filament 4 to be measured parallel to the plane of the detector 1 will give rise to the registry of measurements in the zones 2 and 3, corresponding to the length of the filament 4 during its vibration and displacement and giving rise to a variation corresponding to the variation of length of the filament in the vibratory positions in zones 2 and 3.

According to another characteristic of the invention, the sensitivity of the zones 2 and 3 can be linearly variable or according to another mathematical function, namely exponential, parabolic or the like, as a function of the surface treatment or of the constituents of the zones 2 and 3 themselves. Thus, it is possible to provide the zones 2 and 3 with a conductive or reflecting coating, whose conduction or reflection varies progressively from one edge of one zone to the other edge or even influences directly the material and/or the geometry of the constituents of the zones 2 and 3.

The detector according to the invention can be of the capacitative type, inductive or optical. Thus, the detector according to the invention can be adapted to the measurement of any type of linear product in movement, said product acting as the dielectric, in the case of use of a capacitative detector, and being for example a filament, a yarn, a ribbon or a cloth of a non-conductive material. In the case in which the linear product is a conductive product, the detector can be an inductive detector, the variations of the characteristics of the product having as a result the modification of the magnetic field between the poles of the inductive detector. Finally, in the case in which the detector is in the form of an optical detector, the variations of its illumination by a light source, coherent or not, projected from the side opposite the detector or of the reflected light from a source integrated with said detector or illuminating the product in profile, are gathered in the form of an intensity signal.

In the presence of a capacitative detector, a variation of the morpho-dimensional characteristics of the product, as well as a vibration or a displacement of said product will immediately result in a variation of the dielectric, which can be measured and recorded.

The same is true for an inductive detector used relative to a conductive product and whose magnetic field varies directly as a function of the modifications of the position upon vibration of said product. In the case of use of an optical detector, these are the variations of light intensity which translate the modifications of the morpho-dimensional characteristics of the product and particularly the vibration, and permit delivering a corresponding signal.

According to one characteristic of the invention, the sensitivity of the measurement is obtained by variation of the geometry of the surface of the zones of the detector 1 defined relative to the mean position of the filament 4, in linear fashion or not (FIGS. 1–16). Thus, as shown in FIG. 1, a vibration of the filament 4 to be measured by the detector 1 will permit collecting measurements in the zone of variable geometry, in a first instance in the medial zone, then in the zone 3, in raised position, then in the zone 2, in lowered position. These measurements take account of the length of the filament 4 relative to the surface of the zones 2 and 3 and of the medial zone of the detector 1 facing them. In the case of a surface sensitivity of the variable zones 2 and 3, these latter can have a geometry with parallel edges, namely, for example, rectangular armatures, the vibration being detected in the form of a signal variable as a function of the sensitivity of the occluded zone 2 or 3, without variation of the length of the product present between the armatures.

FIG. 1 of the accompanying drawings shows a first embodiment of the invention, in which the surface 1 forming the detector is in the form of a disc. Thus, vibration of the filament 4 to be measured relative to its axis of movement permits collecting a different signal corresponding to successive measurements in the medial zones 2 and 3 or only in a single zone 2 or 3 and represented by L1 and L2 in FIG. 1. The amplified signal leads to the perception of the vibratory phenomenon, which can be translated by a recordation of the curves corresponding to the series of signals thus collected or to a processing of a series of signals so as to effect a continuous control and/or a regulation.

In the case of the measurement by mass regularity, there appears, during passage of the filament, a disturbance due to vibration, such that, for the measurement of the vibration with a detector according to that of FIG. 1, the sensitivity of this detector to the mass variation gives rise to an important disturbance of the measurement of the vibration.

The invention therefore also has for its object to provide a detector which is independent of variation of the mass and which isolates vibration.

This problem can be resolved by use of a detector in which the displacement of the filament gives rise to a differential response on said detector which has for this purpose elements whose comportment is variable as a function of the position of the filament, but which are mounted in opposition to each other. To this end, there can be provided two detector elements having variable responses as a function of the position of the filament in the detector and which are mounted in opposition of sensitivity. Thus, the correlation of these responses of these two elements gives rise to a variation only if there is displacement in a plane perpendicular to the trajectory of the filament in the field of the detector. The variation of the position will be preponderant relative to the response corresponding to the variation of mass.

Such a variation can be written according to a distribution law f(R) of the sensitivity of the detector, in which:

$$R = \frac{P1 \times C1}{P2 \times C2}$$

in which:

P1 and P2 are morpho-dimensional responses respectively for the zones 1 and 2 of the detector in the evolution of the properties of the zones, which is to say which vary along the length perpendicular to the displacement of the filament in these zones.

C1 and C2 are characteristics of the filament; these characteristics are close if the dimensions of the detector are small.

f(R) is a response law for the regions along the direction perpendicular to the path of movement of the filament and its evolution can be logarithmic, sinusoidal or exponential; by way of example, this law takes account of a variation of capacity, luminous intensity, measurement space, field depth, any vibratory frequency, even a polarization.

This type of detector can also be used to analyze changes in position of characteristics taken from the filament and, by extension, to provide an analysis of all types of movement information, of the shape of the filament, of reflected or diffused light, etc.

FIGS. 2 and 3 of the accompanying drawings show a modified embodiment of the detector according to FIG. 1, in which said detector is constituted, in at least one plane parallel to the median plane of the filament 4 to be measured, by two complementary surfaces 5 separated from each other by an inclined slot 6. Thus, it is possible to effect a comparison of the measurements taken by each surface 5 and, because these surfaces are complementary, to obtain an amplification of the variation of measurement corresponding to one vibration. Thus, one vibration of the filament 4 will give rise, on opposite sides of its mean position while travelling, to the detection, for each surface 5, of a given length, permitting determining for these surfaces 5 a variation of the lengths and, by effecting the ratio of the obtained values, an amplified differential measurement corresponding to one vibration.

In this case, the sensitivity of the detector is adjustable by rotation about its central axis. Thus, one rotation of this detector about its central axis permits a variation of the inclination of the slots separating the two constituent surfaces, such that the vibration measurements collected can be more or less greatly amplified, while maintaining constant the dimensions of the detector that are involved. Thus, one variation by rotation through the angle $\alpha$ between the slot 6 and the axis of movement of the filament from a perpendicular position toward an inclined position in which the angle $\alpha$ is greatly reduced, will have for its result to vary the sensitivity of the detector to the variations of measurement between a value 0 and a very high sensitivity value, the sensitivity being low for a large angle, near 90°, and high for a small angle.

This embodiment permits eliminating the morpho-dimensional variations of the linear product 4. The only important information therefore remains the position of the product 4 relative to the detector.

The obtention of a vibration signal permits, by integration by means of a computer of other data relative to the filament manually displayed or perceived in another manner, to determine the tension of this latter by application of the simplified formula:

$$P = \frac{\pi^2}{l^2}\left[\sqrt{\frac{EIg}{\gamma A}}\,\right]$$

in which:
P: frequency of vibration of the linear product
l: unconfined length of the linear product
E: modulus of elasticity of the material
I: moment of inertia
g: acceleration due to gravity
$\gamma$: specific weight
A: area of the cross section of the linear product.

As a result, knowing the length of the filament along its measurement course, which is to say, for example, between the outlet of a machine and the return to a downstream machine or between two predetermined bearing points disposed on opposite sides of the detector, fixed to this latter or not and adjustable in position or not, its impulses or frequency of vibration and its linear mass determined by its number, it is possible to derive the tension of the filament in operation.

This knowledge of the tension is particularly important in the framework of production of filaments, because during their transformation the applied tensions must be perfectly controlled. During displacement of the filament, there arises a modification of the apparent frequency of vibration for a fixed detector. In the case of a linear product having no vibration, moving or not relative to the detector, there can be provided, as shown in FIG. 3, an excitation device 15 of the electrostatic, mechanical, pneumatic or sonic type, giving rise to a vibration of the filament 4 at its own frequency given by the formula:

$$P = \frac{\pi^2}{l^2}\left[\sqrt{\frac{EIg}{\gamma A}}\,\right]$$

Thus, the vibration imparted to the filament could be measured by the detector.

The contactless length of the path of the filament can easily be determined for a given machine. However, the linear mass and the variations of mass, as well as the speed of movement of the filament, can vary, sometimes quite significantly, such that the tension determined on the basis of the frequency of vibration can be subject to variations incompatible with a correct surveillance of the operation.

To this end, the invention proposes a modified detector permitting simultaneously distinguishing the different parameters, without preliminary entry of any data.

Thus, FIGS. 4–9 show modified embodiments of the detectors according to FIGS. 2 and 3, in which the detector is constituted by a multiplicity of surfaces each permitting an individual measurement and combined treatment, so as to result in a multiple characterization of the moving linear product.

FIG. 4 shows a modified embodiment of the detector according to FIGS. 2 and 3, in which the detector is constituted by two symmetrical polygonal surfaces 5 separated by an inclined slot 6.

The modified embodiment of FIG. 5 corresponds to an embodiment according to FIG. 4, completed by a separation of the detector by a slot 7 which is vertical relative to the moving linear product.

This detector has, as a result, four surfaces 8 to 11 which can be pairwise grouped 8, 11 and 9, 10 diagonally opposed.

As shown in this figure, the surfaces 8 to 11 are of different size, and are separated by a vertical slot 7 and by a diagonal slot 6.

Thus, the detector permits distinguishing, by simultaneous combinations of the measurements taken at each surface 8 to 11, the mass regularity, the vibration and the speed and, by integration of these parameters by means of a computer, the tension according to the simplified formula:

$$P = \frac{\pi^2}{l^2}\left[\sqrt{\frac{EIg}{\gamma A}}\,\right]$$

Thus, the sum of the measurements collected from the surfaces 8 to 11 permits operation of the detector as a conventional detector of morpho-dimensional regularity, known per se. This relative detector can be calibrated, for its use as an absolute detector, in the case in which the material and the conditions of measurements are known. For example, for a capacitative detector, a balance will permit establishing the constant dielectric of the product under the conditions of the test.

The association of the pairs of relative measurements on opposite sides of the diagonal 6, namely the measurements relative to the surfaces 8+9 and 10+11, permits the detection by the differential effect of all the vibrations of the filament. Thus, each lateral displacement of the filament 4 in the air gap of the detector induces an increase of the length of the filament in the portion of the detector formed by the surfaces 8 and 9 and a decrease in the detected length of the filament in the portion of the detector constituted by the surfaces 10 and 11.

By processing the corresponding measurement signals obtained by a Wheatstone half-bridge, it will be possible to derive an output signal corresponding to the vibration.

By the association of the surfaces 8, 10 and 9, 11 or perhaps 8, 10 and 8 to 11, or again 9, 11 and 8 to 11, the surfaces of different lengths or not will permit, as the case may be, a derivation of the speed of movement of the filament by an analysis method using the intercorrelation functions or filtering of the variations of amplitude.

In the embodiment of FIG. 5, the length x of the surfaces 8 and 10 is less than the length x' of the surfaces 9 and 11 and the speed of movement can be derived from a combination of the surfaces 8 and 10 and the surfaces 8 to 11 or 9 and 11, in which the sum of the measurements of the surfaces 8 and 10 will be considered as the electrical signal adapted to be subjected to filtering by comparison with the sum of the measurements of the assembly of the surfaces 8 to 11 or 9 and 11 acting as a filter modifying the shape of the first signal.

By processing the relative amplitudes of the variations, which arise as a function of the length of the measurement field, it is possible to derive the speed of the filament. Thus, by the construction of the detector the length of the field of measurement will be known, such that the emitter signal can be induced.

Thanks to this embodiment, it is possible to carry out an electrical processing of the information permitting obtaining the speed practically in real time, while taking account of the evolution of the sensitivity of the zones 1 and 2, which can for example have a sensitivity of linear development, but in the opposite direction, for example by being in the form of two right triangles disposed head to tail (FIG. 4), or again of sensitivity to development according to another mathematical law, with an exponential, parabolic or other development.

In the case in which the surfaces 8 and 10 and 9 and 11 are separated by a vertical median 7, which is to say when x=x', the use of the intercorrelation functions between the measurements collected at the surfaces 8 and 10 and those collected at the surfaces 9 and 11, will permit calculation of the speed, because the time interval, which separates the identical electrical signals emitted by the combinations of the surfaces 8 and 10 and 9 and 11 and the distance separating the groups of surfaces are known, such that it is possible to determine inevitably the speed of the filament 4.

FIGS. 6 and 7 show modified embodiments of the invention, in which it is possible to collect more than one pair of measurements, namely according to FIG. 6, at least three measurements at each pulsation of the filament 4, and, according to FIG. 7, a multiplicity of measurements, the multiple surfaces being arranged in different manner, symmetrically or by saw-toothed separation, so as to simplify or amplify the signals gathered on the different surfaces, having regard for the shape of these latter.

Figure 8:
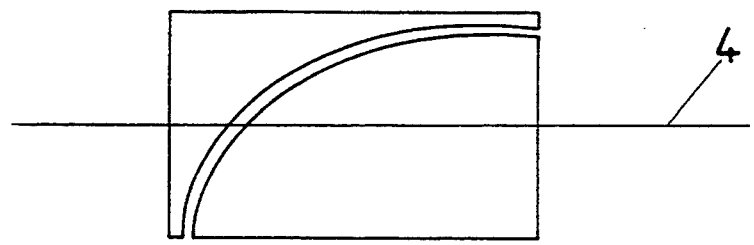

FIG. 8 of the accompanying drawings shows a modified form of the invention, in which the surfaces have a line of separation which can be parabolic, exponential, sinusoidal, cosinusoidal and derivatives thereof. Thus, it is possible to effect a complementary adjustment of the sensitivity of the detector by displacement of the axis of movement of the filament 4 to be measured, perpendicular to said axis of movement. As a result, as a function of this arrangement, the ratios of lengths of the filament from one surface to the other are more or less great and the variation of the length resulting from vibration is more or less amplified.

In this embodiment, the processing of the data is effected in a manner identical to that described with respect to FIG. 2.

Figure 9:
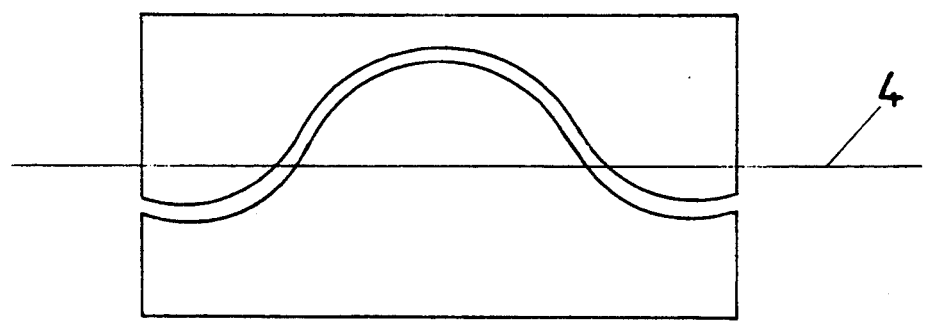

FIG. 9 shows a modified embodiment of FIG. 8, in which the surfaces delimited by the line of separation of parabolic, exponential or other shape, are multiplied, opposed or symmetrical and the processing of the data takes place as in the case of the detector according to FIG. 5. Moreover, the sensitivity of these surfaces can be variable.

Figure 10:
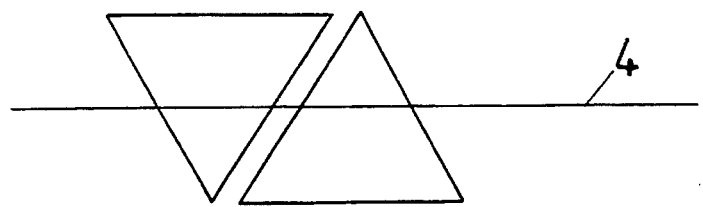

FIG. 10 of the accompanying drawings shows a modified embodiment of the detector according to FIGS. 2 and 3, in which the detector is constituted by two identical surfaces symmetrical relative to a diagonal line.

Figure 11:
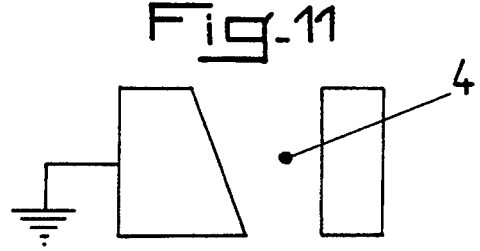
FIGS. 11 and 12 are views analogous to that of FIG. 3, of modified embodiments of the transverse geometry of the detectors.
Figure 12:
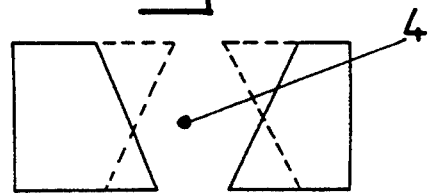

According to another characteristic of the invention, shown in FIGS. 11 and 12, at least one surface 1 of the detector can be inclined relative to the medial plane of the filament 4 to be measured. As a result, it is possible to take a measurement for any plane of the component of vibration of the filament 4. Such a measurement can be a simple measurement, according to the embodiment of FIG. 11, or a differential measurement, according to the embodiment of FIG. 12. In this latter case, the surfaces 1 are inclined symmetrically relative to the medial plane of the axis of movement of the filament 4. Moreover, it is also possible to combine the measurements thus obtained with those obtained by the movement along the successive portions of the surfaces, so as further to increase the sensitivity.

Figure 14:
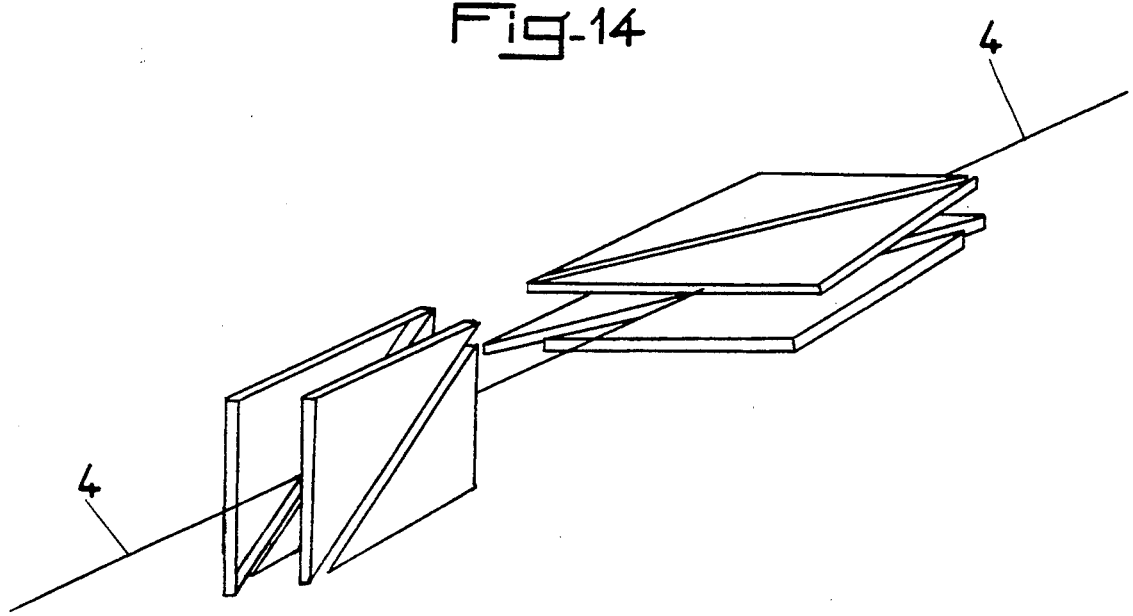
FIG. 14 is a perspective view of another modified embodiment of the invention.

FIG. 14 of the accompanying drawings shows another embodiment of the invention, in which at least two detectors are disposed along the path of the filament, ribbon, yarn or cloth with a rotated offset of 90° relative to each other. Thus, one of the detectors measures the vertical component of the linear product in question and the other its horizontal component.

Figure 13:
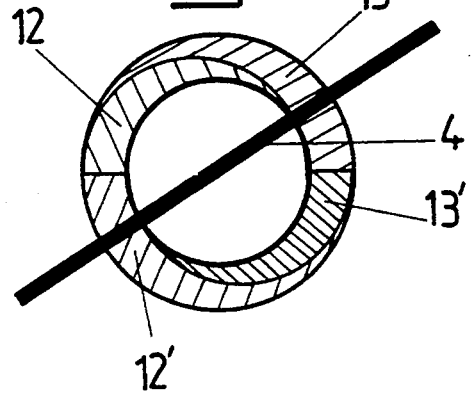
FIG. 13 is a cross-sectional view of a circular and/or tubular detector.

FIG. 13 of the accompanying drawings shows a modified embodiment of the invention, in which the detector is a circular or semicircular detector, or even a tubular or semi-tubular detector, whose sensitive zones 12, 13 and/or 12', 13' extend in opposed semi-crescent shape or concentric semi-circular shape opposite in sensitivity.

In this embodiment, a deviation of the filament relative to its trajectory will give rise to a variation of the length measurements collected in the zones 12 and 13 and perhaps also 12' and 13', which will permit a processing of these data analogous to that effected by means of the detectors particularly of FIGS. 4 and 5.

Moreover, a rotation of the filament 4 about the axis of the detector will result in taking into account a different characteristic of the filament induced by the angle of the filament relative to the detector. This characteristic is detected by the surfaces 12 and 13 and perhaps also by the surfaces 12' and 13'. Thus, the detector according to FIG. 13 permits taking account of the modifications arising from the characteristics of the filament or the like, particularly in the case of a change of direction of this latter about the axis of the detector.

Finally, the surface or surfaces constituting the detector according to the invention, can be provided, in the case of an embodiment such as an optical detector, with optical fibers forming receivers and/or sources of light which is coherent or not and/or reflectors.

Figure 15:
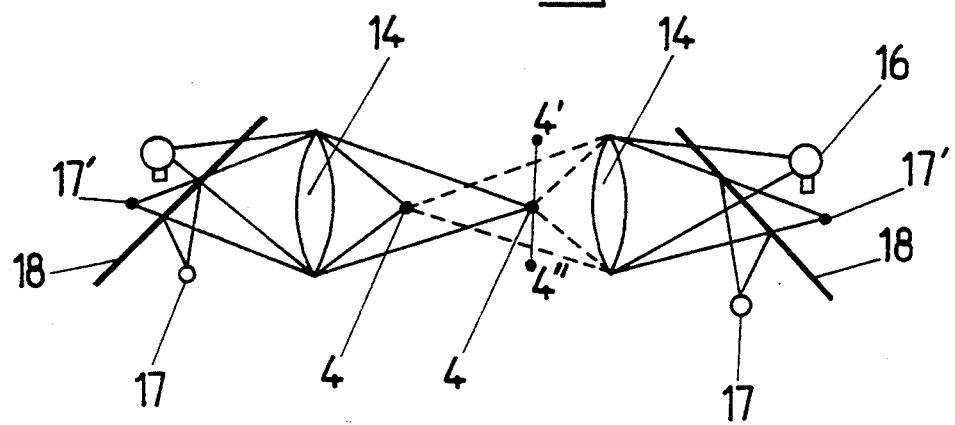

FIGS. 15 and 16 of the accompanying drawings show embodiments of the invention in which the detector is constituted as an optical detector. Thus, FIG. 15 shows an optical detector constituted by two lenses 14 disposed on opposite sides of the linear product 4 to be measured, this product being illuminated by one or two light sources 16 which can be coherent or not and the reflected signal being transferred, in the form of a luminous spot, behind the corresponding lens 14, by means of a semi-reflecting mirror 18, to a corresponding measurement cell 17. Thus, a horizontal displacement of the linear product 4 between the lenses 14 will have as a result a variation of the image detected by the cells 17 and an intercorrelation of the signals collected by these cells will permit defining the variation of the displacement corresponding to the horizontal vibration of the product 4. In the case of a vertical variation, the cells 17 will detect a displacement of the image of the filament 4', 4'', on their sensitive portions According to a modified embodiment of the invention, this detector can be completed by two cells 17' disposed along the axis of the lenses 14 behind the semi-reflecting mirrors 18. These detectors can in particular directly detect a vibration of the filament 4 in the positions 4', 4'' perpendicular to the movement of the filament 4 measured by the cells 17.

FIG. 16 of the accompanying drawings shows another modified embodiment of an optical detector, in which this latter is constituted by a first light source 19 disposed behind a semi-reflective mirror 20 and illuminating through this latter and through a first lens 21 the linear product 4, whose image is reflected by a second semi-reflective mirror 22 disposed between the first lens 21 and the product 4 and transferring said image through a second lens 23, by means of a third semi-reflective mirror 24, onto a first cell 25 for the detection of horizontal vibration, a second light source 26 illuminating the surface of the first semi-reflective mirror 20 opposite the first light source 19 and its light rays being focussed by the first lens 21 and passing through the second semi-reflective mirror 22 to illuminate the product 4 with light waves different from those of the light from the first light source 19, the image of the product 4 obtained being transferred by means of the second semi-reflective mirror 22 through the second lens 23 and the third semi-reflective mirror 24 onto a second cell 27 for detection of the vertical vibration of the product 4. The light sources 19 and 26 preferably emit light rays of respectively different wave lengths λ1 and λ2. The cells 25 and 27 can preferably have a configuration comparable to that of the detector according to FIG. 4.

The detector according to FIG. 16 thus permits effecting, on the one hand, a measurement of the horizontal vibration, which is to say a displacement of the product 4 in a direction perpendicular to the lens 21, consisting in gathering the variations of light energy reflected by the filament differentiated according to the wavelengths λ1 and λ2 of different focal length, and, on the other hand, a measurement of the vertical vibration, which is to say a displacement of the product 4 parallel to the lens 21 and consisting of a displacement of the luminous point reflected and transferred to the second detection cell 27, this point being measured successively on the constituent surfaces of the cell 27, which could have the structure of a detector according to FIGS. 2 to 5.

The use of the detector according to the invention permits the measurement in real time of several data relative to a travelling linear product, without contact with this latter. The measurement signals thus obtained are processed by a program modeling the behavior of the filament according to the simplified formula:

$$P = \frac{\pi^2}{l^2} \left[ \sqrt{\frac{EIg}{\gamma A}} \right]$$

and being stored in a data processing unit of known type, using filters and spectral analyses, so as to eliminate the parasitic signals and to deliver signals proportional to the tension, the speed and regularity, and being adapted to be used as measurement signals to characterize the linear product and its dynamic conditions as measurement, control, regulation or emergency stop or alarm signals.

Moreover, this signal can also be used to display operational data.

When the detector according to the invention is used for regulation or surveillance, it can particularly serve, by the use of an appropriate program, for the modification in the course of operation of certain data relative to the linear product, such as the speed and/or tension, which is particularly important during the accomplishment of certain operations of production, particularly in the field of spinning for the regulation of tension during drawing the fibers and in the field of weaving for control of the tension of the weft threads, during the insertion, as well as the warp threads, during formation of the warp, sizing or weaving.

Moreover, the invention is also applicable in the field of treatment of other linear elements, particularly in the winding of metallic filaments.

Thanks to the invention, it is possible to provide detectors of the capacitative, inductive, optical, phonic or ultrasonic type, permitting simultaneously the contactless measurement of the regularity of the filament, as well as the speed, the vibration and/or the torsion, such that the tension of the filament can be determined by computation.

Finally, the detector according to the invention can, as a function of the principles used, preferably not be constituted by measurement portions or offset active portions, but by superposed portions, the analysis differentiating then the gathered responses.

Of course, the invention is not limited to the embodiments described and shown in the accompanying drawings. Modifications remain possible, particularly from the point of view of the construction of the various elements, or by substitution of technical equivalents, without thereby departing from the scope of protection of the invention.

We claim:

1. Detector for the measurement of the characteristics of a linear product of very great length relative to its other dimensions, on a production machine, wherein said detector operates without contact with said linear product and is provided with at least one means (1) having zones (2 and 3) for a measurement relative to a mean position of said linear product and measuring one of the variation of the complex morpho-dimensional and positional characteristics of said linear product, this latter varying, either by vibratory movement, or by induced displacement of the mean position of the axis of movement, the measuring zones (2 and 3) each having a different and variable sensitivity relative to the medial plane of the axis of said linear product to be measured.

2. Detector, according to claim 1, wherein a sensitivity of the measurement zones (2 and 3) is variable according to one of a linear, exponential, or parabolic function, said sensitivity also being variable of at least one a function of a surface treatment and material of said zones (2 and 3).

3. Detector according to claim 1, wherein said measurement zones (2 and 3) are provided with one of a conductive and a reflective coating, said conductive and reflective coatings varying progressively from one edge of a zone to another edge of said zone.

4. Detector, according to claim 1, wherein the sensitivity of the measurement zones (2 and 3) is variable by direct modification of at least one of the material and the geometry of the constituents of said zones (2 and 3).

5. Detector, according to claim 1, wherein said detector is one of a capacitative, inductive and optical type detector.

6. Detector, according to claim 1, wherein the sensitivity of the measurement zones (2 and 3) varies relative to the geometry of the surface of said zones defined relative to a mean position of the filament (4), in one of a linear and non-linear manner.

7. Detector, according to claim 1, wherein a surface of said detector is in the shape of a disc.

8. Detector, according to claim 1, wherein said detector is constituted, in at least one plane parallel to the medial plane of the linear product to be measured (4), by two complementary surfaces (5) separated from each other by an inclined slot (6).

9. Detector, according to claim 8, wherein the sensitivity of the detector is adjustable by rotation about a central axis of said detector.

10. Detector, according to claim 1, further comprising an excitation device (15), of one of an electrostatic, mechanical, pneumatic and sonic type, said excitation device producing vibration of the linear product at a predetermined frequency.

11. Detector, according to claim 1, wherein said detector comprises a plurality of surfaces each permitting an individual measurement and a combined treatment, so as to allow a multiple characteristic of the moving linear product to be measured.

12. Detector, according to claim 1, wherein said detector is constituted by two symmetrical polygonal surfaces (5) separated by an inclined slot (6).

13. Detector, according to claim 11, further comprising, in at least one plane parallel to the medial plane of the linear product to be measured, two complementary surfaces separated from each other by an inclined slot and by a slot (7) which is vertical relative to the moving linear product (4), so as to form four surfaces (8 to 11) separated by said inclined slot and said vertical slot that can be grouped pairwise (8, 11 and 9, 10) in diagonal opposition.

14. Detector according to claim 11, wherein said detector is constituted by at least two surfaces having a separation line having one of a parabolic, exponential, sinusoidal, cosinusoidal and derivative shape.

15. Detector, according to claim 14, wherein the surfaces are symmetrical.

16. Detector, according to claim 1, wherein said detector is constituted by two identical surfaces that are symmetrical relative to a diagonal line.

17. Detector, according to claim 1, wherein said at least one means (1) is inclined relative to a medial plane of the linear product to be measured.

18. Detector, according to claim 17, wherein said means (1) is inclined symmetrically relative to the medial plane of the axis of movement of the linear product.

19. Detector, according to claim 1, wherein said detector is combined with at least one second detector, the two detectors being disposed on the path of one of the linear product, a ribbon, a roving and a cloth, said two detectors being disposed at a rotational offset of 90° relative to one another.

20. Detector, according to claim 1, wherein said detector has one of circular, semi-circular, tubular, and semi-tubular shape and has sensitive regions (12, 13 and/or 12', 13') extending in one of a semi-crescent and concentric semi-circular shape, said sensitive regions having opposite sensitivity.

21. Detector, according to claim 1, wherein the surface of the detector is provided with optical fibers forming at least one of receivers and sources of light which is one of coherent and not coherent and reflectors.

22. Detector, according to claim 1, wherein said detector is an optical detector comprising by two lenses (14) disposed on opposite sides of the linear product (4) to be measured, said linear product being illuminated by one of one and two sources (16) of light that is one of coherent and not coherent and signals reflected from said illuminated linear product being partially reflected, as luminous spots, onto a measurement cells (17) by means of semi-reflective mirrors placed behind said two lenses (14).

23. Detector, according to claim 22, wherein said detector comprises two cells (17') disposed on an axis of the lenses (14) behind the semi-reflective mirrors (18).

24. Detector, according to claim 1, wherein said detector is an optical detector comprising a first light source (19) disposed behind a first semi-reflective mirror (20) and illuminating through this semi-reflective mirror and a first lens (21) the linear product (4), whose image is reflected on a second semi-reflecting mirror (22) disposed between the first lens (21) and the linear product (4) and transferring said image through a second lens (23), by means of a third semi-reflective mirror (24) onto a first cell (25) for the detection of horizontal vibration, a second light source (26) illuminating the surface of the first semi-reflective mirror (20) opposite the first light source (19) and light rays of said second light source being focussed by the first lens (21) and passing through the second semi-reflective mirror (22) to illuminate the linear product (4) with light waves of a wavelength different from the wavelength of the light emitted from the first light source (19), the image of the product (4) obtained being transferred by means of the second semi-reflective mirror (22) through the second lens (23) and the third semi-reflective mirror (24) onto a second cell (27) for the detection of the vertical vibration of the linear product (4).

* * * * *